United States Patent [19]

Hosaka et al.

[11] 4,021,495

[45] May 3, 1977

[54] PURIFICATION OF β-NAPHTHOL

[75] Inventors: Hirokazu Hosaka, Hirakata; Kunihiko Tanaka, Ibaraki; Yuji Ueda, Izumiotsu, all of Japan

[73] Assignee: Sumitomo Chemical Company, Limited, Osaka, Japan

[22] Filed: June 18, 1975

[21] Appl. No.: 588,117

[30] Foreign Application Priority Data

June 19, 1974 Japan ............................. 49-70506

[52] U.S. Cl. .................. 260/621 A; 260/621 C; 260/624 A; 260/627 G
[51] Int. Cl.$^2$ ......................................... C07C 39/14
[58] Field of Search .......... 260/621 A, 621 B, 627, 260/624 A, 621 C, 627 G, 627 R; 40/7

[56] References Cited

UNITED STATES PATENTS

| | | | |
|---|---|---|---|
| 2,470,116 | 5/1949 | Swietoslawski et al. | 260/674 |
| 2,727,927 | 12/1955 | Vriens et al. | 260/621 A |
| 2,771,491 | 11/1956 | Conner | 260/610 B |
| 2,776,322 | 1/1957 | Webster et al. | 260/621 A |
| 2,985,687 | 5/1961 | Thelin et al. | 260/621 |

*Primary Examiner*—James O. Thomas, Jr.
*Assistant Examiner*—W. B. Lone
*Attorney, Agent, or Firm*—Sughrue, Rothwell, Mion, Zinn & Macpeak

[57] ABSTRACT

A process for purifying crude β-naphthol obtained via an alkylnaphthalene hydroperoxide, comprising subjecting the crude β-naphthol to a recrystallization treatment using (1) an aliphatic or alicyclic hydrocarbon solvent having 5 to 10 carbon atoms, or (2) a mixed solvent comprising the aliphatic or alicyclic hydrocarbon solvent and at least one other solvent selected from the group consisting of benzene, a benzene derivative, a ketone, an alcohol, an ether and an ester.

7 Claims, No Drawings

PURIFICATION OF β-NAPHTHOL

BACKGROUND OF THE INVENTION

1. Field of the Invention

The present invention relates to a purification of crude β-naphthol obtained via an alkylnaphthalene hydroperoxide, and more particularly it relates to a method for efficient removal of by-products, including α-naphthol, which are difficult to separate by conventional methods from the crude β-naphthol.

2. Description of the Prior Art

At present, the most common method for preparing β-naphthol is a sulfonation of naphthalene followed by fusion. However, many problems are now encountered with this method in terms of manufacturing cost, mass productivity and pollution control measures. Recently, a new industrially advantageous synthetic method for preparing β-naphthol via an alkylnaphthalene hydroperoxide is attracting attention in this field. The alkyl group referred to herein for the alkylnaphthalene hydroperoxide includes an isopropyl, sec-butyl and cyclohexyl group, of which the isopropyl group is most common. Therefore, hereinafter the description will be given in terms of isopropylnaphthalene hydroperoxide.

This method of synthesis of β-naphthol via an isopropylnaphthalene hydroperoxide comprises three reaction steps.

1. The first step is a preparation of isopropylnaphthalene from two starting materials, naphthalene and propylene, in the same manner as in the preparation of cumene from benzene and propylene. For example, the reaction can be conducted using aluminum chloride as a catalyst at 50° C to 150° C.

2. The second step is an oxidation of the isopropylnaphthalene thus obtained to isopropylnaphthalene hydroperoxide (referred to as N-HPO hereinafter) with oxygen or an oxygen-containing gas at 70° to 120° C in the presence of an alkali.

3. The last step is a cleavage of the N-HPO thus obtained into β-naphthol and acetone by treating the N-HPO at 50° to 120° C in the presence of an acid catalyst such as sulfuric acid.

In this process, the reaction product after the cleavage contains acetone, α-naphthol, isopropylnaphthalene, isopropenylnaphthalene, acetylnaphthalene, dimethylnaphthyl carbinol (which is easily dehydrated to isopropenylnaphthalene at a relatively high temperature) and a tarry material in addition to β-naphthol. Of these by-products, acetone can easily be removed by distillation since acetone has a boiling point greatly different from those of the other by-products. Isopropylnaphthalene and isopropenylnaphthalene can also be removed relatively easily by rectification or other operations. However both α-naphthol and acetylnaphthalene have a boiling point very close to that of β-naphthol and moreover have a very high boiling and melting point. More specifically, the boiling points of α-naphthol and β-naphthol are 288° C/760 mmHg and 295° C/760 mmHg, respectively, and the melting points are 96° C and 123° C, respectively. Thus, it has been considered to be very difficult to separate β-naphthol alone in a high purity by rectification from a mixture with these by-products. In other words, the preparation of β-naphthol via the hydroperoxide route has been considered to be very impractical as an industrial process, unless an advantageous purification of β-naphthol from the cleavage product could be established.

In this process via the hydroperoxide, it is unavoidable for β-isopropylnaphthalene to be contaminated with a certain amount of α-isopropylnaphthalene produced as a by-product. Therefore, the resulting hydroperoxide is also a mixture of α- and β-isomers, resulting in the formation of α-naphthol as a by-product in the last reaction step.

Consequently, for the purpose of producing β-naphthol industrially advantageously, it is desirable to control the content of the α-isopropylnaphthalene in the β-isomer used as a material for oxidation to as low a level as is possible. Previously, a process was found in which the production of α-isopropylnaphthalene as a by-product could be controlled to a small extent, but preparation of the β-isomer alone is impossible industrially and contamination of the β-isomer with a certain amount of the α-isomer can hardly be avoided. Therefore, α-N-HPO is also produced by oxidation and thus the resulting naphthol from the cleavage is a mixture of α- and β-isomers. This means that purification of β-naphthol from the cleavage product requires removal of α-naphthol from the β-isomer thereof.

Separation of β-naphthol by a countercurrent extraction process is disclosed in U.S. Pat. No. 2,727,927, but removal of α-naphthol which is a serious problem is very difficult by this process.

Furthermore, U.S. Pat. No. 3,076,035 discloses a method for separating β-naphthol from a mixture of the α-isomer and the β-isomer by subjecting the mixture to a recrystallization treatment using an aqueous sodium hydroxide solution. However, this method is not advantageous from the standpoint of cost since a large amount of sodium hydroxide is used and moreover the after-treatment is so troublesome that the method can not be employed industrially.

SUMMARY OF THE INVENTION

A process for purification of β-naphthol by removal of various impurities, particularly the α-naphthol produced as a by-product in the preparation of β-naphthol via the hydroperoxide route was extensively studied, and it has now been found that recrystallization from a specific organic solvent is a very efficient purification of β-naphthol, and can very easily be employed industrially.

The present invention provides a purification process of crude β-naphthol obtained via an alkylnaphthalene hydroperoxide, comprising recrystallizing the β-naphthol using (1) an aliphatic or alicyclic hydrocarbon having 5 to 10 carbon atoms, or (2) a mixture of the above aliphatic or alicyclic hydrocarbon and one or more solvents selected from the group consisting of benzenes, ketones, alcohols, ethers and esters.

DETAILED DESCRIPTION OF THE INVENTION

It was discovered that the selection of the solvent is the most important factor in the recrystallization method, although other factors can of course not be neglected, and that requirements of the solvent used for purification of β-naphthol by recrystallization must be as follows:

1. high recovery of β-naphthol,
2. capability of selectively dissolving either β-naphthol or the impurities only, thus enabling a complete removal of, particularly, α-naphthol and acetylnaphthalene, which are similar to β-naphthol in physical properties, and
3. easy recrystallization operation.

As for requirement (1), even if recovery of the β-naphthol is low in one operation, β-naphthol can theoretically be obtained in a high recovery by repeating the recrystallization operation. However, an increasing number of recrystallizations increases the number of apparatuses and makes the operation more troublesome, therefore it is desirable in terms of efficiency to obtain β-naphthol in a high recovery with as low a number of recrystallizations as possible.

As for the requirement (2), even if the capability of selective dissolution is low an increase in purity can be achieved by repeating the recrystallization but such can not be said to be efficient. Furthermore, there are some cases where a high purity can not be theoretically achieved even by repeating the recrystallization due to the presence of an eutectic point.

As for requirement (3), the crystal form of the β-naphthol separated is essential. If the crystal form is difficult to filter, the filtration time is prolonged and the content of the mother liquor in the filter cake increases so that the required purity can not be achieved. Furthermore, an increase in the content of the crystals in the slurry increases the viscosity of the slurry and makes the handling of the slurry more difficult. Accordingly, a solvent in which β-naphthol is soluble is unsuitable.

The crude β-naphthol which is used in the recrystallization is a product obtained by subjecting the oxidation product of isopropylnaphthalene to an acidic cleavage. Usually, it is more preferred to use the acidic cleavage product from which low boiling components such as acetone, pre-fractions such as isopropylnaphthalene and isopropenylnaphthalene, and tarry materials have been removed to some extent by distillation or other operations than to use the cleavage product as it is. Particularly, it is most preferred in terms of the treating operation and the recovery efficiency to control the content of the α-naphthol as an impurity to less than about 10% by weight based on the β-naphthol.

This is also the case with other impurities. Although pure β-naphthol can be obtained using the present recrystallization process even if the content of each of the iso-propylnaphthalene, isopropenylnaphthalene, dimethylnaphthyl carbinol, acetylnaphthalene and tarry material in the crude β-naphthol is about 20 to 30% by weight based on the weight of the β-naphthol, contamination with a large amount of these impurities causes a decrease in recrystallization efficiency. Therefore it is preferred for the present recrystallization to control the content of each of these materials to less than about 10% by weight. It is most advantageous for an industrial scale operation to use a crude β-naphthol in which the total content of the by-products to be removed is less than about 40% by weight based on the weight of the β-naphthol.

The aliphatic or alicyclic hydrocarbons having 5 to 10 carbon atoms which are used in process of the present invention include for example, n-pentane, n-hexane, isohexane, n-heptane, n-octane, isooctane n-decane, petroleum ether, petroleum benzin, ligroin, cyclohexane and methylcyclohexane. Of these solvents, those solvents having higher boiling points are more preferred since the amount used can be decreased.

In the present invention, the recrystallization can of course be carried out using these aliphatic or alicyclic hydrocarbon solvents alone, but these solvents must be used in a relatively large amount because of the low solubility of the β-naphthol in these aliphatic or alicyclic hydrocarbons. On the other hand, a large amount of solvent is not required with benzene series solvents, but recovery of the β-naphthol tends to decrease to some extent. Therefore, the combined use of benzene series solvents and aliphatic or alicyclic solvents is very effective because this makes it possible to not only reduce the amount of solvent used but also to achieve high recovery in the recrystallization. Furthermore, a solvent selected from the group consisting of a ketone, an alcohol, an ether and an ester is not suitable as a solvent for the present recrystallization. However, when such a solvent is used together with at least one of the above-described aliphatic or alicyclic hydrocarbons, the solvent mixture is also very effective because the mixture has a desirable effect on the reduction in the total amount of solvent required and improvement in recovery.

Thus, the present invention can also be carried out using an aliphatic or alicyclic hydrocarbon and at least one other solvent as described above.

Examples of benzene series solvents include benzene or substituted benzenes substituted with one to three alkyl groups having 1 to 4 carbon atoms, for example, benzene, toluene, xylene, ethylbenzene, diethylbenzene, cumene and cymene. Examples of ketones include acetone, methyl ethyl ketone, methyl n-propyl ketone, methyl isopropyl ketone, and methyl isobutyl ketone; of alcohols include methanol, ethanol, propanol and ethylene glycol; of ethers include diisopropyl ether, diethyl ether and ethylene glycol monoethers such as the monoethyl ether and the monomethyl ether; and of esters include methyl acetate, ethyl acetate, propyl acetate, butyl acetate and ethylene glycol monoesters such as the monoacetate ester. Of the abovementioned solvents, toluene, diisopropyl ether and methyl isobutyl ketone are particularly effective.

As described above, various combinations of solvents are possible, but mixing too many types of solvents is very disadvantageous from a practical standpoint, because the separation and recovery of the solvents are very complicated and troublesome. Therefore, advantageous solvent systems are a one-component system comprising the aliphatic or alicyclic hydrocarbon alone, or a two-component system comprising the aliphatic or alicyclic hydrocarbon and a solvent selected from the group consisting of benzene or its derivatives, ketones, alcohols, esters and ethers.

The recrystallization treatment in the present invention comprises (1) mixing the molten crude β-naphthol containing impurities with a solvent as defined above while stirring, dissolving the β-naphthol and impurities completely and then cooling the solution or (2) mixing crude β-naphthol crystals which were previously ground for ease of dissolution in the solvent, dissolving the crystals completely while heating and then cooling.

A pre-heating of the solvent is effective in terms of operational efficiency.

Furthermore, in some cases a satisfactory result can be obtained, even if the crude β-naphthol is not completely dissolved in the solvent, that is, some of the β-naphthol crystals remain undissolved, according to the special conditions of size of crystals, kind of solvents and temperature.

The amount of solvent used depends upon the kind of solvent and temperature. The amount generally is about 1 to 20 times by weight based on the weight of the crude β-naphthol, preferably 3 to 10 times by weight. The amount of the other solvent mixed with the aliphatic or alicyclic hydrocarbon is preferably up to 30% by weight based on the weight of the aliphatic or alicyclic hydrocarbon.

The temperature at which the crude β-naphthol is dissolved is suitably selected depending upon the kind and amount of solvents, and is generally within the range of from about 80° C to the reflux temperature of the solvent or solvent mixture employed.

The temperature at which crystals are separated is suitably selected depending upon the kind and amount of solvents, and generally ranges from about −20° C to about 50° C, preferably about 0° to about 30° C in terms of ease of operation and efficiency of recrystallization.

The above-described range can be selected of course, to be within the most suitable range according to the kind and amount of solvents, dissolution temperatures and cooling temperatures.

As an apparatus for recrystallization, common reaction vessels, and conventional rotary type heat exchangers, for example, a Votator (made by Girdler Corp., U.S.A.) can be used.

The thus obtained slurry containing β-naphthol crystals can be separated into the crystals and solvent using conventional methods, for example, filtration. Where filtration is employed centrifugal filtration is more efficient.

In general, the β-naphthol thus obtained can be used per se as a final product, but if desired they may be washed or recrystallized repeatedly.

The recovery of the β-naphthol which is achieved by the recrystallization of crude β-naphthol according to the present invention depends upon the content of impurities including α-naphthol, but generally the recovery is as high as about 90 to 98% per recrystallization operation.

According to the process of the present invention, it is possible to obtain β-naphthol having a purity of higher than 99.5%. The β-naphthol thus obtained is in the form of a powder (granules) or needles. The product can be dried as it is as the final product, or it can be converted to a flake form.

The present invention will be illustrated with reference to the examples, which are only given for the purpose of illustration and are not to be interpreted as limiting. Unless otherwise indicated herein, all parts, percents, ratios and the like are by weight.

EXAMPLE 1

Crude naphthol obtained using the method via isopropylnaphthalene hydroperoxide which contained 890 g of β-naphthol, 40 g of α-naphthol, 20 g of isopropylnaphthalene, 20 g of acetylnaphthalene and 30 g of tarry material was melted and added to 12,000 g of cyclohexane with stirring. The mixture was heated to 80° C until the crude naphthol was completely dissolved and then cooled to 0° C gradually during which crystals separated. By centrifugal filtration, 929 g of crystals were obtained. On distillation, the solvent contained in the crystals was first removed and then 851 g of distillate were obtained. The purity of the β-naphthol was 99.4% and the recovery of the β-naphthol was 95%.

EXAMPLE 2

Crude naphthol containing 870 g of β-naphthol, 40 g of α-naphthol, 20 g of isopropylanaphthalene, 20 g of acetylnaphthalene and 40 g of tarry material was melted and added to a mixed solvent comprising 6,300 g of n-heptane and 700 g of toluene with stirring. The mixture was heated to 101° C until the crude naphthol was completely dissolved and then cooled to 10° C gradually. The separated crystals were filtered with a centrifuge. 927 g of crystals containing 844 g of β-naphthol were obtained. The β-naphthol obtained by distillation had a purity of 99.5% and the β-naphthol recovery was 97%.

EXAMPLE 3

Crude naphthol containing 800 g of β-naphthol, 80 g of α-naphthol, 20 g of isopropylnaphthalene, 20 g of isopropenylnaphthalene, 20 g of acetylnaphthalene and 40 g of tarry material was powdered and added to a mixed solvent comprising 5,000 g of n-heptane and 1,200 g of methyl isobutyl ketone. The mixture was heated to 97° C until the crude naphthol was completely dissolved, cooled to 0° C gradually and then filtered. 802 g of crystals were obtained and 726 g of purified β-naphthol was obtained on drying. The purity of the β-naphthol was 99.2% and the recovery was 90%.

EXAMPLE 4

Crude naphthol obtained using the method via isopropylnaphthalene hydroperoxide which contained 880 g of β-naphthol, 50 g of α-naphthol, 20 g of isopropylnaphthalene, 10 g of isopropenylnaphthalene, 20 g of acetylnaphthalene and 30 g of tarry material was melted and added to 10,500 g of n-heptane under stirring. The mixture was heated to 95° C until the crude naphthol was completely dissolved and then gradually cooled to 0° C during which crystals separated. By centrifugal filtration, 905 g of crystals were obtained. On distillation, the solvent contained in the crystals was first removed and then 833 g of distillate was obtained. The purity of the β-naphthol was 99.3% and the recovery of the β-naphthol was 94%.

REFERENCE EXAMPLE 990 parts of the same crude β-naphthol as used in Example 2 were melted and added to 1,300 parts of ethanol under stirring, and the mixture was heated while stirring until the crude naphthol was completely dissolved. Then the solution was gradually cooled to 0° C with crystals separating. The mixture was then filtered using a centrifuge. 923 parts of the crystals were obtained with 230 parts being ethanol as a solvent. Therefore, it can be said that centrifugal removal of the mother liquor is not good. The crystals were dried to remove the ethanol and the β-naphthol thus obtained had a purity of 96.1% and contained 1.4% of α-naphthol, 0.3% of isopropylanphthalene and 0.6% of acetylnaphthalene. The recovery of the β-naphthol obtained as crystals was 77.0%.

While the invention has been described in detail and with reference to specific embodiments thereof, it will be apparent to one skilled in the art that various changes and modifications can be made therein without departing from the spirit and scope thereof.

What is claimed is:
1. A process for purifying crude β-naphthol obtained via an alkylnaphthalene hydroperoxide route, comprising heating said crude β-naphthol using (1) a saturated aliphatic or alicyclic solvent having 5 to 10 carbon atoms, or (2) a mixed solvent comprising said saturated aliphatic or alicyclic hydrocarbon and at least one other solvent selected from the group consisting of benzene, toluene, xylene, ethylbenzene, diethylbenzene, cumene, cymene, acetone, methyl ethyl ketone, methyl n-propyl ketone, methyl isopropyl ketone, methyl isobutyl ketone, methanol, ethanol, propanol, ethylene glycol, di-isopropyl ether, diethyl ether, ethylene glycol monoether, methyl acetate, ethyl acetate, propyl acetate, butyl acetate and ethylene glycol monoester to a temperature not higher than the reflux temperature of said hydrocarbon solvent or solvent mixture employed, and separating the resulting crystals of β-naphthol at a temperature of −20° to 50° C, the amount of said hydrocarbon solvent or solvent mixture being about 1 to 20 times by weight based on the weight of the crude β-naphthol.

2. The process according to claim 1, wherein said crude β-naphthol contains α-naphthol, isopropylnaphthalene, isopropenylnaphthalene, dimethylnaphthyl carbinol, acetylnaphthalene and a tarry material as impurities.

3. The process according to claim 2, wherein the total content of said impurities is less than about 40% by weight based on the weight of the β-naphthol.

4. The process according to claim 2, wherein the content of the α-naphthol is less than about 10% by weight based on the weight of the β-naphthol.

5. The process according to claim 1, wherein said aliphatic hydrocarbon is n-pentane, n-hexane, isohexane, n-heptane, n-octane, isooctane, n-decane, petroleum ether, petroleum benzin, ligroin, cyclohexane or methylcyclohexane.

6. The process according to claim 1, wherein the amount of the other solvent mixed with the aliphatic or alicyclic hydrocarbon is up to about 30% by weight based on the weight of the aliphatic or alicyclic hydrocarbon.

7. The process according to claim 1, wherein said recrystallization comprises (a) mixing said crude β-naphthol and said hydrocarbon solvent or said mixed solvent at about 80° C to the reflux temperature of said solvent, (b) cooling said mixture to about −20° C to about 50° C to form a slurry and (c) filtering said slurry.

* * * * *